Figure 1:
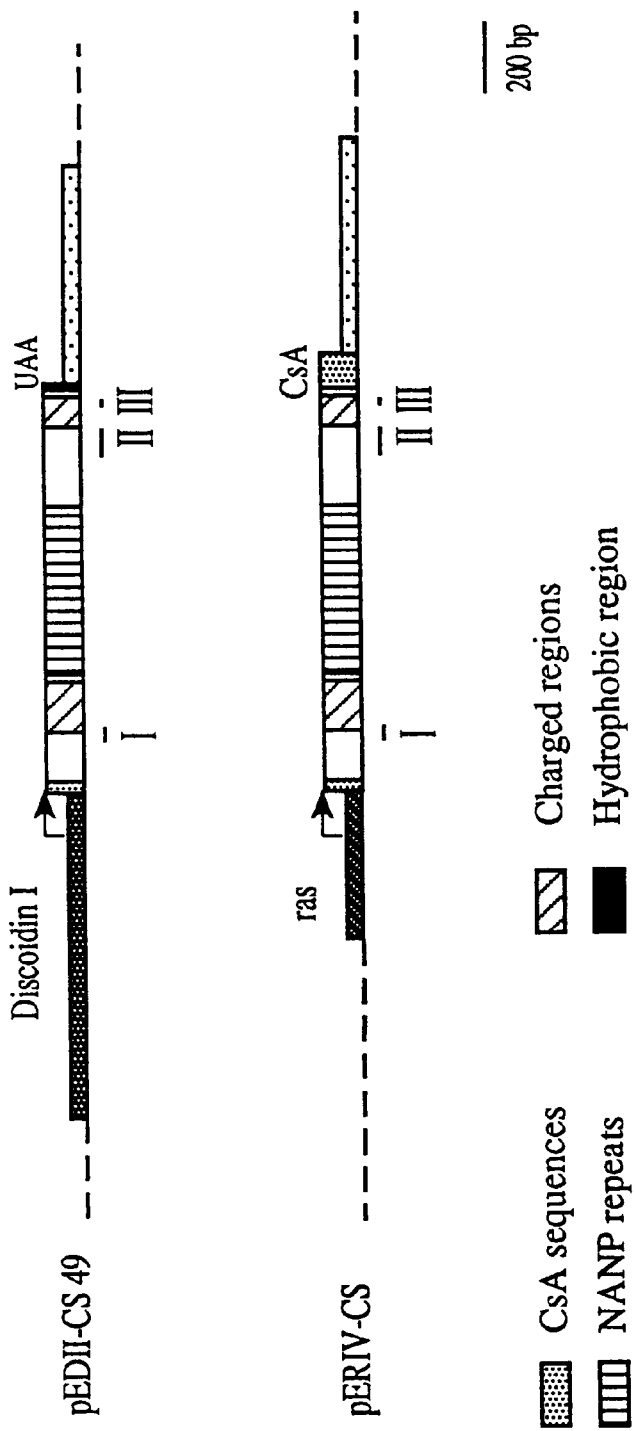
Figure 2:
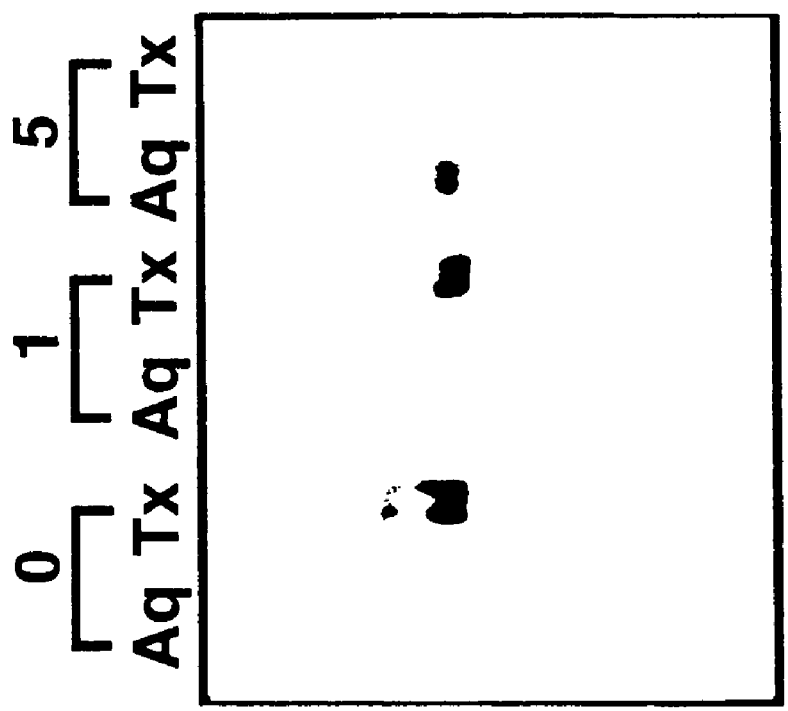

United States Patent [19]
Fasel et al.

[11] Patent Number: 6,113,917
[45] Date of Patent: *Sep. 5, 2000

[54] MODIFIED POLYPEPTIDES FOR ENHANCED IMMUNOGENICITY

[75] Inventors: Nicolas Joseph Fasel, Epalinges; Christophe Dominique Reymond, Prilly, both of Switzerland

[73] Assignee: RMF Dictagene S.A., Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/428,616

[22] Filed: Apr. 25, 1995

[51] Int. Cl.$^7$ .................. A61K 39/00; A61K 39/002; A61K 39/015; C12P 21/06

[52] U.S. Cl. ................. 424/268.1; 424/184.1; 424/192.1; 424/265.1; 424/269.1; 424/272.1; 435/69.1; 435/71.1; 435/69.7; 435/71.2

[58] Field of Search .............. 424/184.1, 192.1, 424/265.1, 268.1, 269.1, 272.1; 435/69.1, 71.1, 69.7, 71.2

[56] References Cited

U.S. PATENT DOCUMENTS 5,543,323   8/1996   Ridley et al. .................. 435/252.3

FOREIGN PATENT DOCUMENTS 9220806   11/1992   WIPO.
WO 95/22614   8/1995   WIPO.

OTHER PUBLICATIONS

Reymond et al, Journal of Biological Chemistry 270 (21):12941–12947, 1995 (May 26).

Barth et al. Journal of Cell Biology 142(1–2):205–215, 1994.

Pearce, et al., "Three Major Surface Antigens of *Schistosoma mansoni* Are Linked to The Membrane By Glycosylphosphatidylinositol", The Journal of Immunology, vol. 142, No. 3, Feb. 1, 1989, pp. 979–984.

Reymond, et al., "Anchóring of an Immunogenic *Plasmodium falciparum* Circumsporozoite Protein on the Surface of *Dictyostelium discoideum*", The Journal of Chemistry, vol. 270, No. 21, May 26, 1995, pp. 12941–12947.

Pearce et al. J. of Immunology 142(3):979–984, 1989.

De–Majumdan, Experimental Parasitology 74:251–260, 1992.

Haynes et al. Eur. J. Biochem 216:729–737, 1993.

Saito et al. Eur. J. Biochem 218:623–628, 1993.

Michael Good along with Eleanor Riley. Immunology Today 13(4):126–130, 1992.

Brown KN Nature 331(27):300, 1984.

Beghadidi–Rais et al. J. Cell Sci 105(3):831–840, 1993.

Moran et al. Journal of Cell Biology 125(2):333–343, 1994.

Fasel et al Gene 111:157–163, 1992.

*Primary Examiner*—James C. Housel
*Assistant Examiner*—V. Ryan
*Attorney, Agent, or Firm*—Cushman Darby & Cushman

[57] ABSTRACT

A recombinant polypeptide comprising a polypeptide which has added thereto a glycoxyl-phosphatidylinositol anchor structure, said polypeptide demonstrating a greater immune response than the corresponding polypeptide without the anchor. The polypeptide may be a parasite antigen such as a *Plasmodium falciparum* polypeptide. Recombinant vectors comprising the DNA sequence encoding the polypeptide with a glycolipid anchor addition sequence and host cells based thereon are also disclosed as well as vaccines and methods of inducing an immune response based on the polypeptides.

7 Claims, 2 Drawing Sheets

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 77 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

```
ATGTCTAGAT TTTTAGTATT GATAATATTA TATAATATTT TAAATAGTGC ACATTCAGCT      60

CCAACCCAGG ATCCATG                                                    77
```

(2) INFORMATION FOR SEQ ID NO:2:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

```
ACCCAGGATA CCCTTATTCC AG                                              22
```

(2) INFORMATION FOR SEQ ID NO:3:

(i) SEQUENCE CHARACTERISTICS:
       (A) LENGTH: 37 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

```
AAAGCCGAGC TCTTAATTAA GGAACAAGAA GGATAAT                              37
```

(2) INFORMATION FOR SEQ ID NO:4:

(i) SEQUENCE CHARACTERISTICS:
       (A) LENGTH: 39 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

```
CCCGGTACCA GGCCTGATAT CTCCAACTCC AACTGAAAC                            39
```

(2) INFORMATION FOR SEQ ID NO:5:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (ii) MOLECULE TYPE: DNA (genomic)

```
        (xi) SEQUENCE DESCRIPTION: SEQ ID NO:5:

CGGCTCGAGT TAAATTAATA AAACAAAAGA AATG                                    34

(2) INFORMATION FOR SEQ ID NO:6:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:6:

CCCGGTACCA TTATTCCAGG AATACCAGTG C                                       31

(2) INFORMATION FOR SEQ ID NO:7:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:7:

ATAGGCCACA TTTTTCCATT TTACAAATTT TTTTTTC                                 37
```

MODIFIED POLYPEPTIDES FOR ENHANCED IMMUNOGENICITY

The present invention relates to modified polypeptides showing enhanced immunogenicity, in particular to polypeptides modified by a lipidic structure. In particular it relates to parasite polypeptides modified by a lipidic structure and more particular to the circumsporozoite protein of *Plasmodium falciparum* modified by such a lipidic structure. The invention further relates to a method for inducing an immune response against the modified polypeptides, to a method, vector and host for producing the polypeptides and to vaccines comprising the polypeptide.

The immune system is complex and not fully understood. The way by which foreign immunogens are recognized by the host immune system is only partially elucidated. The immune response of mammals exposed to foreign proteins varies to a large extend. Any method to prepare polypeptides with increased immunogenicity is therefore of great interest, overcoming otherwise weakly immunogenic epitopic sites.

One way to improve vaccination with recombinant proteins was to produce multiple epitopic sites from more than one protein originating from one or multiple infectious agents. This approach allows to obtain less expensive polyvalent, more efficient vaccines leading to simpler and safer immunization regimens. However, such an approach implies that every polypeptide is produced in sufficient amounts, requiring specific purification protocols for each polypeptide used for immunization insuring optimal quantity. It is challenging to find approaches where a strong immune response against specific epitopes is induced whereas the immunogens are in low quantity or present in a mixture of other polypeptides like it is observed in certain in vivo situations.

*Plasmodium falciparum*, the most frequent malaria causative agent, is found in different forms in insect and human hosts. The use of inactivated parasite forms as vaccine in mammals has shown promising results. A major limitation, however, is the fact that sporozoites cannot be cultivated and have to be isolated from mosquito salivary glands precluding the use of inactivated parasite as such to obtain protection.

To circumvent this problem, genes encoding specific proteins of different Plasmodium forms have been expressed in heterologous recombinant systems and used as potential host protective antigens, with limited success. Alternatively, peptides corresponding to defined regions of the antigens have been used in protection studies, showing the limitation of such immunizations. The circumsporozoite protein (CSP) is one of the antigens present at the surface of the *Plasmodium falciparum* sporozoite found in the organism after insect bite transmission. This protein is synthesized as a polypeptide precursor composed of an amino terminal signal sequence removed upon processing, of a large central repeat doman flanked on both side by regions referred as region I and region II containing conserved sequences between different Plasmodia species and of an hydrophobic terminal carboxy domain. The repeat domain NANP consisting of a tandem repeat of the amino acid cluster asparagine-alanine-asparagine-prolins ((ASN-ALA-ASN-PRO)$_n$) has been shown to be an effective B-cell epitope of *P. falciparum* CSP. Synthetic peptides containing such a repeat have been used with limited success as subunit vaccine in protection studies. The T-cell response elements on the CSP protein have been mapped outside the repeat segments. In every experiment so far, the immunization experiments have been performed with large amounts of purified antigens.

It is the object of the present invention to provide modified proteins, such as *Plasmodium falciparum* proteins, which can elicit a strong immune response even if the parasite antigens are not purified. This approach is interesting for the future developments of whole cell vaccines allowing less expensive not efficient immunization regimens.

According to the invention it has now been found that the addition of a glycosyl phosphatidylinositol (GPI) anchor to an antigen elicits a higher immune response than the corresponding antigen without the anchor.

The invention therefore provides recombinant polypeptides showing enhanced immunogenicity, comprising a glycosyl-phosphatidylinositol structure for eliciting an increased immune response as compared to corresponding polypeptides without the anchor. The polypeptide may be an antigen, preferably a parasite antigen, such as a *Plasmodium falciparum* antigen, like the *P. falciparum* circumsporozoite protein (CSP) or modified versions thereof.

In the description and the claims the use of the phrase "or modified versions thereof" intends to incorporate any derivative of the circumsporozoite protein showing sufficient immunogenicity to induce an immune response. Therefore not only the complete protein, but also fragments or mutated versions thereof are included.

The invention is illustrated herein by reference to the CSP protein of *P. falciparum*. However, the invention is not limited to this particular antigen. For the skilled person it will be a matter of routine to substitute the CSP by other desirable antigens thus obtaining the advantages of the invention without undue experimentation. The invention being based on the insight that the addition of a GPI-anchor to any polypeptide enhances the immunogenicity thereof.

Expression of CSP has been obtained in heterologous recombinant systems (*E. coli*, yeast, Vaccinia virus, baculovirus, *Salmonella*, *Dictyostelium discoideum*). It has been found that species of the slime mold Dictyostelium can be used as an efficient eukaryotic expression system for the production of recombinant proteins. Furthermore, compared to other expression systems, a complete stable CSP polypeptide may be produced in Dictyostelium (Fasel, N., Begdadi-Rais, C., Bernard, M., Bron, C., Corradin, G., and Raymond, C. D., (1992) *Gene*, 111, 157–163). This system can thus be used to obtain a stronger and longer lasting immune protection since the complete CSP carries every B- and T-cell epitope.

Furthermore, Dictyostellium has biotechnological potential. It is a free-living organism, easy to grow and to maintain. Strains can grow on bacteria lawns with a doubling time of about 3 hours, in bacterial suspensions to high densities (up to $10^{10}$ cells per liter) or in a semi-synthetic media containing glucose, peptone and yeast extract where doubling time is about 12 hours.

The life cycle of Dictyostelium consists of a growth and of a developmental phase. The developmental phase is triggered by starvation and is characterized by aggregation of previously single cells to form a multicellular organism which then differentiates to produce spores. In the presence of bacteria or rich medium spores germinate, leading to renewed growth. During this developmental cycle, diffusible factors are produced and for at least one of them (cAMP) binding to its receptor induces transcription of a set of specific genes (see Loomis, The Development of *Dictyostelium discoideum*, Acad. Press, 1982). Growth properties and transformation capacity of *Dictyostelium discoideum* offers the possibility to express foreign proteins, since cells can be grown at low cost on bacteria and expression of specific proteins can be tightly controlled by starvation in a simple medium. Finally, Dictyostelium discoideum is a safe, non-toxic, non-pathogenic free-living organism which could be a candidate for whole cell vaccine development if not for human at least for veterinary use.

Dictyostelium discoideum may thus be used for the production of the modified polypeptides of the invention, by transformation of the cells with a suitable vector, culturing the cells under circumstances allowing the expression of the polypeptide and optionally isolating the polypeptide. A suitable vector comprises a DNA sequence encoding the polypeptide, which DNA sequence is operatively linked to a glycolipid anchor addition sequence located downstream thereof, and suitable transcription initiation and termination sequences operatively linked thereto. The DNA sequence preferably encodes a parasite antigen, such as a Plasmodium falciparum antigen, like the P. falciparum circumsporozoite protein (CSP) or modified versions thereof.

Many cell surface proteins in various organisms are anchored in the membrane lipid bilayer by a glycosyl phosphatidylinositol (GPI) structure. This complex structure is synthesized as a precursor glycolipid and transferred onto glycoproteins in the endoplasmic reticulum. The transfer of the preformed GPI anchor onto specific polypeptides is possible only if the appropriate signal sequence (herein also referred to as "glycolipid anchor addition sequence") is contained in the C-terminal region of target proteins. This signal sequence has been shown to be composed of a group of 10–12 residues upstream of a hydrophobic C-terminal sequence. In Dictyostelium, specific proteins have been shown to be anchored by a GPI. The C-terminal sequence determinants have been defined for one of these proteins, namely Contact site A (noegel, A., Gerisch, G., Stadler, J. and Westphal, M. (1986) EMBO J. 5, 1473–1476). The GPI anchor once transferred to the polypeptide can be cleaved by specific phospholipases (GPI-phospholipase C or D), leading to a modification of the hydrophobic nature of the protein as detected by a different partitioning in a particular detergent, TX-114.

According to the invention the recombinant DNA vector therefore comprises a glycolipid anchor addition sequence which is derived from the D. discoideum contact site A.

The invention further provides for a method of producing antibodies directed to one or more epitopes of a polypeptide, which method comprises the immunization of a suitable (e.g. mammalian) host with the polypeptide of the invention and optionally the subsequent isolation of the antibodies thus produced. As an alternative whole serum may be used. Preferably the polypeptide for immunization takes the form of a whole cell lysate of a host cell expressing the polypeptide.

In this invention as an example, an immune response in mice was elicited by injecting whole cell lysates of Dictyostelium expressing glycosyl phosphatidylinositol anchored CSP. Furthermore, a specific immune response was obtained only when the CSP epitopes were linked to GPI, showing a potentiation of the immune response.

Furthermore, the present invention relates to a vaccine for immunization of mammalian hosts. The vaccine comprises the modified polypeptide of the invention in an immunoprotective amount, together with a suitable excipient. The immunoprotective amount comprises for example the polypeptide content of about $1-5 \times 10^7$, in particular $2 \times 10^7$ host cells transformed with a vector encoding the polypeptide and the glycolipid anchor addition sequence.

The following example illustrates the present invention, but should not be considered as limiting the scope thereof.

EXAMPLE

1. Introduction

The following example teaches the production of Plasmodium falciparum CSP modified by addition of a glycolipid anchor in Dictyostelium discoideum and its use in immunization regimens. In more detail, the CSP polypeptide was expressed in the slime mould Dictyostelium discoideum by fusing a leader peptide and a glycosyl-phosphatidylinositol (GPI) addition signal sequence derived from the Dictyostelium contact site A.

Mice were immunized with Dictyostelium whole cell lysates expressing this GPI modified polypeptide. The antibodies raised recognized two different regions of the polypeptide. Thus, GPI modified polypeptides can be expressed in Dictyostelium cells. Both the polypeptides in isolated form and the cells comprising the polypeptides may be used in immunization protocols having potentials for vaccination, diagnostic tests or basic studies.

2. Material and methods

For the following experiments use is made of many techniques well known and accessible to those skilled in the art of molecular biology, protein chemistry and immunology. Such methods are not always described in details.

Enzymes are obtained from commercial sources and used according to supplier's protocols.

Bacterial media and current cloning techniques are described in Sambrook et al. (Molecular cloning: A Laboratory Manual, CSH press 1989)

Monoclonal antibodies and $NANP_{50}$ were obtained from F. Sinaglia (Hoffman La Roche Ltd, Basel)

3. Constructions of CS containing plasmids 3.1. pEDII-CS 49

Expression vector pEDI-CS is constituted of the pVEII vector (Naniak and Nellen, (1990) Nucl. Acids Res. 18, 5375) which contains the elements important for propagation and maintenance in a prokaryotic host (origin of replication and ampicillin resistance gene) and of a Tn903 encoded neomycin resistance gene conferring geneticin (G418) resistance to eukaryotic cells under the control of a Dictyostelium actin 15 transcription unit. The presence of a Discoidin 1 promotor allows the developmental control of expression of downstream sequences and actin 8 sequences insure proper termination of the RNA.

For construction of the pEDI-CS expression vector the HaeIII+RsaI restriction fragment of 1161 bp of the CS NF54 gene (Caspers, P., Gentz, R., Matile, H., Pink, J. R., and Sinigaglia, F. (1989) Mol. Biochem. Parisitol. 35, 185–189) was first inserted into the Asp718+BamHI site of pVEII, after filling in by Klenow DNA polymerase. Subsequently both DNA strands of a sequence encoding the contact site A (CsA) leader peptide plus 3 amino acids were synthesized on an Applied Biosystem Model, 380 B DNA synthesizer. The nucleotide sequence of the synthetic leader peptide is as follows:

5'-ATGTCTAGATTTTTAGTATTGATAATATTATATA
ATATTTTAAATAG
TGCACATTCAGCTCCAACCCAGGATCCATG-3'
(SEQ ID NO:1)

and was confirmed by introducing the blunt end fragment into M13mp18 replicative form at the SmaI site, followed by DNA sequencing.

The XbaI/BamHI restriction fragment containing the CsA leader peptide was then isolated and inserted at the XbaI/BamHI sites present in the vector to generate expression vector pEDII-CS. In the pEDII-CS expression vector, the natural UAG stop codon of the CSP was replaced by the UAA stop codon. This was done by replacing most of the CSP coding region by a DNA fragment amplified using specific oligonucleotides as follows:

5' amplimer (placed downstream of the CsA leader peptide sequence and containing a BamHI site):

5'-ACCCAGGATACCCTTATTCCAG-3' (SEQ ID NO:2)

3' amplimer (corresponding to the last codons of the CSP gene but containing an UAA stop codon and a SacI site):

5'-AAAGCCGAGCTCTTAATTAAGGAACAAGAAG GATAAT-3' (SEQ ID NO:3)

These oligonucleotides carry specific restriction sites, BamHI and SacI, which are also present in the pEDII-CS and were used to replace the CSP gene segment of pEDII-CS. Using this strategy we obtained the expression vector pEDII-CS49 which produces a CSP protein with its original C-terminal polypeptide.

3.2. pERIV-CS

To express a GPI modified form of the CSP the plasmid pERIV-CS was constructed. This plasmid is derived from pERIV which itself is derived from pERII, a plasmid which is a combination of a Dictyostelium ras promoter fragment, a CsA signal peptide, an actin 6 termination sequence and of a neoR cassette in a pGEM3 vector. The neoR cassette, which comprises a Dictyostelium actin 15 promoter, the bacterial Tn903 resistance gene and a Dictyostelium actin 15 termination sequence were isolated from pDneo2 (Witke, W., Nellen, W., and Noegel, A. (1987). *EMBO J.* 6, 4143–4148) using EcoRV and inserted into pGEM3 (Promega corp.). The Dictyostelium ras promoter-CsA signal peptide fragment from pERI-CS (Fasel et al., supra) was then inserted in between the EcoRI and BamHI sites. The actin 6 termination sequence extracted from pDneo2 had first to be cloned into the HindIII site of pGEM4 (Promega corp.) to provide a second BamHI site, then to be re-isolated and inserted into BamHI site located next to the CsA signal peptide. The construct containing the actin 6 termination sequence in the proper orientation was called pERII. This plasmid was digested by EcoRV+XhoI and a DNA fragment obtained by amplification of a region coding for the glycosyl phosphatidylinositol anchor addition sequence was inserted using the appropriate sites. The two oligonucleotides used in the amplification have the following sequence:

5' amplimer (contains the EcoRV site):

5'-CCCGGTACCAGGCCTGATATCTCCAACTCC AACTGAAAC-3' (SEQ ID NO:4)

3' amplimer (contains an XhoI site):

5'-CGGCTOGAGTTAAATTAATAAAACAAAAGA AATG-3' (SEQ ID NO:5)

The pERIV plasmid was digested by Asp718+EcoRV and the CSP NF54 allele was inserted. The CSP DNA, comprising the CSP gene but excluding the N-terminal signal peptide and the C-terminal hydrophobic CSP encoding segments, was obtained by amplification using the following amplimers:

5' amplimer (contains Asp718 site):

5'-CCCGGTACCATTATTCCAGGAATACCAGTGC-3' (SEQ ID NO:6)

3' amplimer (contains an HaeIII site which can be fused to the EcoRV site):

5'-ATAGGCCACATTTTTCCATTTTACAAATTTTT TTTTC-3' (SEQ ID NO:7)

The amplified DAN was inserted, after digestion with Asp718 and HaeIII between the Asp718 and EcoRV sites of pERIV. The plasmid obtained was designated pERIV-CS.

4. Dictyostelium cell culture, transformation and expression

Dictyostelium cells were cultured in shaking suspensions in HL-5 medium up to $5 \times 10^6$ cells/ml and starved in PDF (Pad Dilution Fluid) (Sussman, M. (1987) *Methods in Cell Biology* (Spudich, J. A., ed.) pp 9–29, Acad. Press, Inc., Orlando, Fla.). The various vectors were introduced by electroporation and expressing cells were selected as described in (Nellen, W., and Firtel, R. A. (1985) *Gene* 39, 155–163; Howard, P. K., Ahern, K. G., and Firtel, A. (1988) *Nucleic Acids Res.* 16, 2613–1623).

For Discoidin I promoter dependent expression, *D. discoldeum* cells were starved for 4 hours in shaking suspension (160 rpm) in PDF at a density of $5 \times 10^6$ cells/ml unless otherwise indicated (Fasel et al, supra).

For ras promoter constructs, the cells were starved for 6 hours in PDF at about $5'10^6$/ml and transcription was induced by addition of 200 μM cAMP and 10 nM DIF (Differentiation Inducing Factor) (Morris, H. R., Taylor, G. W., Massento, M. S., Jermyn, K. A., Kay, R. R. (1987), Nature 328, 811–814) for one hour unless otherwise stated (Louvien, J. F., Scholder, J. C., Pinaud, S., and Reymond, C. D. (1911) *Nucleic Acids Res.* 19, 6133–6138).

5. Protein analysis

The proteins from $2 \times 10^6$ cells (per 4 mm wide slot), boiled in 1× Laemmli buffer for 5 min, were separated by 10% SDS-PAGE (Sambrook, J., Fritsch, E. F., and Maniatis, T. (1989) *Molecular cloning: a laboratory manual.*, 2nd Ed., Cold Spring Harbor Laboratory, Cold Spring Harbor, N.Y.). Proteins were electrotransferred onto nitrocellulose (Immunoblots). Fifty μg per ml of the anti-NANP monoclonal antibody (Sp3E9) (Boulanger, N., Matile, H., and Betschart, B. (1988) *Acta. Tropica* 45, 55–65) was added to the filter and incubated overnight at room temperature. Alkaline phosphatase conjugated protein A and chemiluminescence reaction (Amersham) were used to reveal anti-NANP binding.

6. GPI-phospholipase D assay

The GPI-PLD sensitivity of CSP modified with GPI was tested by lysing pERIV-CS cells in 20 mM Tirs/HCl pH 7.5, 0.1M $CaCl_2$, 0.008% TX-100 by four cycles of freezing and thawing. One or 5 units of GPI-PLD enzyme (Boehringer Mannheim) was added and the extracts incubated for 1 hour at 37° C. TX-114 in 1× TBS containing 1 mM EDTA was then added to a final concentration of 1% and the aqueous and detergent phases were separated. The samples were resolved on a 10% SDS polyacrylamide gel and analyzed by immunoblotting using the Sp3E9 monoclonal antibody as previously described.

7. ELISA

Serum and monoclonal antibodies produced against the N-terminal (amino acids 22–125), the NANP repeat peptide, or the C-terminal (amino acids 289–390) segment peptides were assayed by ELISA. Briefly, vinyl plates were coated with different peptides, washed and blocked with 1% BSA in PBS. Monoclonal or serum antibodies were serially diluted in 1% BSA/PBS containing 0,05% Tween 20. Diluted sera were added to antigen coated wells and incubated for 1 hour at room temperature. Plates were washed with PBS containing 0.5% Tween 20 and an appropriate dilution of peroxidase-conjugated species specific anti-IgG was added and incubated for 1 hr at room temperature. One hundred microliters of peroxidase substrate solution were added to each well and the A410 was determined. The end point of ELISA titers for the mice sera was designed to be the serum dilution producing an absorbance value 2 SD greater than the average of the control mice.

8. Immunization of animals and analysis of the antisera

Two times 25 µl or one time 50 µl of a 1:1 sonicated mixture of incomplete Freund's adjuvant and 2×10⁷ cells were injected into Balb/c mice either subcutaneously or intraperitoneally, respectively. After 4 weeks, a boost was performed with an equivalent material, sera were collected 10 days afterwards, and analyzed by ELISA.

9. Results

For the development of a live vaccine, or diagnostic test, CSP modified by a GPI was expressed. The CSP-terminal hydrophobic segment (last 23 amino acids) was thus replaced by the last 49 amino acids of the Contact site A (CsA) polypeptide containing a GPI anchoring domain (Noegel et al., supra) (FIGS. 1A and B). The CSP/CsA fusion gene was inserted under the control of the ras promoter (Louvion et al., supra, Fasel et al., supra). The construct was introduced into *D. discoideum* cells (pERIV-CS). Immunofluorescence using anti-CSP antibodies was used to ascertain presence of CSP at the surface of pERIV-CS cells (data not shown). Due to the use of the ras promoter, only 20 to 40% of the induced cells showed expression, which were those differentiating into prestalk cells (Reymond, C. D., Gomer, R. H., Mehdy, C., and Firtel, R. A. (1984) *Cell* 39, 141–149).

The CSP/CsA fusion protein produced in *Dictyostelium discoideum* has the amphiphilic character expected for a GPI modified protein (Bordier, C. (1981) *J. Biol. Chem* 256, 1604–1607, Conzelmann, A., Spiazzi, A., Hyman, R., and Bron, C. (1986) *EMBO J.* 5, 3291–3296) since it partitions in the TX-114 detergent phase (FIG. 2). To confirm the presence of a GPI anchor on the CSP/CsA fusion protein, the cells were lysed by 3 cycles of freezing and thawing in 0.008% TX-100 and the cell lysates treated for 1 hour with 1 or 5 units of GPI-PLD. Removal of the lipidic portion of the CSP/CsA with 5 units of GPI-PLD altered its hydrophobic character and provoked its partitioning into the aqueous phase (FIG. 2), whereas incubation with 1 unit had a limited effect. These results indicate the presence of a GPI structure on CSP expressed in Dictyostelium cells, thus indicating that *D. discoideum* can produce, process and modify heterologous parasite proteins by additing a GPI anchor.

To assess the ability of the GPI modified CSP to induce an immune response, 8 Balb/c mice were immunized subcutaneously or intraperitoneally with $2\times10^7$ whole cells mixed with incomplete Freund's adjuvant. Ten days after a second injection, the humoral immune response was analyzed by ELISA against synthetic peptides from different regions of the CSP (Table 1). Antibodies were detected against the immunodominant NANP repeat region, against the C-terminal non repetitive region (amino acids 289–390), but not against the N-terminal 22–125 synthetic peptide. Interestingly, presence of specific antibodies and antibody titers were not influenced by the route of injection (Table 1). As control experiments mice were injected with Dictyostelium cells expressing the CSP synthesized by the pEDII-C849. In this case, the CSP has its original peptidic C terminal segment and is not modified by a GPI anchor. No antibodies directed against different segments of CSP (Table 2) were detected in ELISA.

10. Figure legends

FIG. 1 Circumsporozoite protein (CSP) expression vectors A. A detailed description on the general of these two vector is given in the text. Briefly, CSP lacking its first 18 amino acids was fused in frame to the CsA leader peptide leading to pEDII-CS and replacement of the original *P. falciparum* UAG to UAA resulted in construct pEDII-CS 49. pERIV-CS was derived from pERII (see text) which contains the Tn5 neoR gene between actin 15 promoter and termination sequences. The GPI anchoring domain of the CsA protein was placed in frame at the C-terminus of CSP (see panel B). Symbols: "Discoidin I" and "ras" are sequences promoting transcription in Dictyostelium. Arrows indicate transcription start sites. I, II and III indicate highly conserved domains of the CSP.

B. In pERIV-CS, the CSP hydrophobic domain was replaced by the last 49 amino acids of the CsA protein. An extra proline (P) was added during cloning between the CSP (underlined) and CsA sequences.

FIG. 2. Phospholipid modification of CSP expressed in Dispoideum cells

Proteins extracted from about $2\times10^6$ cells were treated by GPI-PLD with 1 (lanes 1) or 5 units for one hour (lanes 5), submitted to a TX-114 phase separation (Bordier, supra) and analyzed by immunoblot. Briefly, stably transformed cells were lysed and separated by SDS PAGE and proteins were transferred onto nitrocellulose. CSP was revealed by immunodetection using $(NANP)_{50}$ monoclonal antibody Sp3E9. The apparent molecular mass of the CSP (62 kDa) was estimated using molecular mass standards. Molecular mass standards were as follows: phosphorylase b (97 kDa), bovine serum albumin (66 kDa), egg white ovalbumin (42.7) kDa). Aq: Aqueous phase, Tx: TX-114 detergent phase. O: samples not treated by GPI-PLD.

11. Tables

TABLE 1

ELISA of sera[a] of pERIV-cs immunized mice with $(NANP)_{50}$, M1 (189–390) peptides.

| Animal | $(NANP)_{50}$ ELISA titer | M1 (289–390) ELISA titer |
|---|---|---|
| B(ip)[b] | 1/1000 | 1/900 |
| G(sc) | 1/5000 | 1/900 |
| R(ip) | 1/5000 | 1/900 |
| Y(sc) | 1/1000 | 1/300 |
| Y(ip) | 1/5000 | 1/300 |
| W(ip) | 1/1000 | 1/900 |
| Control[c] | <1/10 | <1/10 |

[a]sera were obtained 7 days after a single boost of Balb/c mice immunized with 2 × $10^7$ cells
[b]mice were immunized either subcutaneously (sc) or intraperitoneally (ip)
[c]control animal was injected with incomplete Freund's adjuvant alone

TABLE 2

Elisa of sera[a] of pEDII-CS 49 immunized mice with $(NANP)_{50}$, M1 (289–390) and M2 (22–125) peptides.

| Animal | $(NANP)_{50}$ ELISA titer | M1 (289–390) ELISA titer | M2 (22–125) ELISA titer |
|---|---|---|---|
| Nr. 1[b] | <1/10 | <1/10 | <1/10 |
| Nr. 2 | <1/10 | <1/10 | <1/10 |
| Nr. 3 | <1/10 | <1/10 | <1/10 |
| Control[c] | <1/10 | <1/10 | <1/10 |

[a]sera were obtained 7 days after a single boost of Balb/c mice immunized with 2 × $10^7$ cells
[b]mice were immunized either subcutaneously (sc) or intraperitoneally (ip)
[c]control animal was injected with incomplete Freund's adjuvent alone

What is claimed is:

1. An immunogenic composition comprising i) a recombinant polypeptide comprising an immunogenic polypeptide which had added thereto a ceramide based lipid-glycan anchor structure as a result of fusing said polypeptide to the last 49 amino acids of the contact site A protein, said recombinant polypeptide demonstrating a greater immune response than the corresponding polypeptide without the anchor structure, and ii) a suitable excipient.

2. The immunogenic composition of claim 1 wherein the polypeptide is an antigen.

3. The immunogenic composition of claim 2 wherein the antigen is a parasite polypeptide.

4. The immunogenic composition of claim 3 wherein the parasite polypeptide is a Plasmodium polypeptide.

5. The immunogenic composition of claim 4 wherein the polypeptide is a *Plasmodium falciparum* polypeptide.

6. The immunogenic composition of claim 5 wherein the *Plasmodium falciparum* polypeptide is circumsporoite protein (CSP).

7. The immunogenic composition of claim 1, wherein the recombinant polypeptide is expressed in a Dictyostelid host.

* * * * *